(12) United States Patent
Knight

(10) Patent No.: US 12,164,581 B2
(45) Date of Patent: *Dec. 10, 2024

(54) ON-LINE SYSTEM AND METHOD FOR SEARCHING RECIPES FOR MEAL PLANNING

(71) Applicant: 7262591 Canada Ltd., Ottawa (CA)

(72) Inventor: Chris Knight, Ottawa (CA)

(73) Assignee: 7262591 Canada Ltd., Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,796

(22) Filed: Jun. 30, 2023

(65) Prior Publication Data

US 2023/0342406 A1    Oct. 26, 2023

Related U.S. Application Data

(63) Continuation of application No. 17/258,814, filed as application No. PCT/CA2019/050851 on Jun. 17, 2019, now Pat. No. 11,727,070.

(60) Provisional application No. 62/695,257, filed on Jul. 9, 2018.

(51) Int. Cl.
| | |
|---|---|
| *G06F 16/9532* | (2019.01) |
| *G06F 16/9535* | (2019.01) |
| *G06F 16/9538* | (2019.01) |
| *G16H 20/60* | (2018.01) |

(52) U.S. Cl.
CPC ...... *G06F 16/9532* (2019.01); *G06F 16/9535* (2019.01); *G06F 16/9538* (2019.01); *G16H 20/60* (2018.01)

(58) Field of Classification Search
CPC ............ G06F 16/9532; G06F 16/9535; G06F 16/9538; G16H 20/60
See application file for complete search history.

(56) References Cited

U.S. PATENT DOCUMENTS

| | | | | |
|---|---|---|---|---|
| 5,983,200 | A * | 11/1999 | Slotznick | G06Q 30/0621 |
| | | | | 705/28 |
| 9,639,805 | B1 * | 5/2017 | Feller | G06F 40/30 |
| 9,797,873 | B1 * | 10/2017 | Feller | G01N 33/00 |
| 10,402,920 | B2 * | 9/2019 | Fox | G06Q 50/12 |
| 10,595,660 | B2 * | 3/2020 | Patadia | A47J 27/04 |
| 2002/0026363 | A1 * | 2/2002 | Dunaway, Jr. | G06Q 30/02 |
| | | | | 705/15 |

(Continued)

OTHER PUBLICATIONS

PCT Office, Search Report and Written Opinion issued in PCT/CA2019/050851 mailed on Aug. 21, 2019.

(Continued)

*Primary Examiner* — Mark E Hershley
(74) *Attorney, Agent, or Firm* — Wood Herron & Evans LLP

(57) ABSTRACT

Embodiments relate to a system and method to plan preparation of a meal that may include more than one dish. Online recipes are obtained from a database based on criteria set by the user. Recipes are analyzed for time and effort requirements at each step. If a meal includes more than one dish, a merge of the timelines is performed to determine if it is feasible to prepare all dishes concurrently. Suppliers that can supply all ingredients required by the recipes that meet all user criteria are recommended to the user.

13 Claims, 9 Drawing Sheets

(56) References Cited

U.S. PATENT DOCUMENTS

| | | | | |
|---|---|---|---|---|
| 2003/0158796 | A1* | 8/2003 | Balent | G06Q 30/06 705/28 |
| 2006/0036395 | A1* | 2/2006 | Shaya | G16H 20/60 702/127 |
| 2008/0235097 | A1* | 9/2008 | Armstrong | G06Q 50/12 705/15 |
| 2009/0024605 | A1* | 1/2009 | Yang | G06F 16/9535 707/999.005 |
| 2010/0034935 | A1* | 2/2010 | Wally | A47J 37/00 426/232 |
| 2010/0049578 | A1* | 2/2010 | Salerno | G06Q 50/12 705/16 |
| 2010/0313768 | A1* | 12/2010 | Koether | A47J 36/321 99/325 |
| 2011/0055044 | A1* | 3/2011 | Wiedl | G06Q 30/0282 705/347 |
| 2011/0213667 | A1* | 9/2011 | Lerullo | G06Q 30/02 434/219 |
| 2012/0136751 | A1* | 5/2012 | Ochtel | G06Q 30/0633 715/810 |
| 2013/0149677 | A1* | 6/2013 | Slone | G09B 19/0092 434/127 |
| 2013/0185646 | A1* | 7/2013 | Wiggins | H04L 67/62 715/739 |
| 2014/0101233 | A1* | 4/2014 | Mina | G06F 16/972 709/203 |
| 2014/0272816 | A1* | 9/2014 | Callahan | G06Q 30/0633 434/127 |
| 2014/0272817 | A1* | 9/2014 | Park | G09B 5/02 434/127 |
| 2015/0208858 | A1* | 7/2015 | Robbins | A47J 27/002 426/231 |
| 2015/0220603 | A1* | 8/2015 | Bhatt | G06F 40/284 707/722 |
| 2015/0334785 | A1* | 11/2015 | Visher | H05B 6/065 219/626 |
| 2016/0203192 | A1* | 7/2016 | Bhattacharjya | G06F 16/2457 707/769 |
| 2017/0018041 | A1* | 1/2017 | Fox | G06Q 20/3224 |
| 2017/0061392 | A1* | 3/2017 | Meza-Guinea | G06Q 50/12 |
| 2017/0316488 | A1* | 11/2017 | Kremen | G09B 5/06 |
| 2018/0133900 | A1* | 5/2018 | Breazeal | B25J 19/026 |
| 2018/0232689 | A1* | 8/2018 | Minvielle | G06T 7/194 |
| 2018/0284735 | A1* | 10/2018 | Cella | G05B 23/0264 |
| 2018/0284747 | A1* | 10/2018 | Cella | G05B 23/0264 |
| 2019/0279281 | A1* | 9/2019 | Kumar | G06Q 30/0631 |
| 2020/0121125 | A1* | 4/2020 | Zito | A47J 37/12 |

OTHER PUBLICATIONS

U.S. Patent and Trademark Office, Office Action issued in U.S. Appl. No. 17/258,814 dated Jan. 4, 2022.
U.S. Patent and Trademark Office, Office Action issued in U.S. Appl. No. 17/258,814 dated Aug. 29, 2022.
U.S. Patent and Trademark Office, Office Action issued in U.S. Appl. No. 17/258,814 dated Jan. 20, 2023.

* cited by examiner

200

User Interface
300

210 Constraint(s) can't be met

Ingredient Extraction
400

220 Constraint(s) met

Ingredient Aggregation
205

Supplier Selection
500

Output
600

Figure 2

ON-LINE SYSTEM AND METHOD FOR SEARCHING RECIPES FOR MEAL PLANNING

FIELD OF INVENTION

The disclosure relates generally to natural language processing and machine learning. More specifically, embodiments provide techniques to plan the preparation of a meal by applying text analytics and machine learning approaches to online recipes.

BACKGROUND

A recipe usually includes multiple steps, some of which require active involvement from the recipe user and others require no or minimal attention from the recipe user. Frequently a recipe user is looking to prepare a meal of several dishes (e.g. an appetizer, a main course, and dessert) within a specific time period (e.g. a maximum of 6 hours). While many recipes provide total preparation time and total cooking time, they do not indicate the timeline of the individual steps. When a user selects potential recipes to prepare for a meal, he will need to determine if it is feasible to prepare all the dishes concurrently and within the desired time frame, based on the description of the steps. If it is not feasible, the user will have to substitute one or more of the potential recipes and carry out the analysis all over again. For users with limited experience or practice in meal preparation, such an exercise could be daunting.

Recipes are typically unstructured text. A particular task can be described in different ways. Furthermore, the time required for each task may not be stated and needs to be inferred. For example, one of the steps of a roasted vegetables recipe involves chopping of 4 different vegetables into pieces. An experienced user would estimate washing and chopping of the vegetables will take 30 minutes. Such time estimation is not usually stated explicitly in a recipe.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an on-line system and method for searching recipes for meal planning. In accordance with an aspect of the present invention, there is provided an on-line system for searching recipes for meal planning, the system comprising a memory that stores program code, a processor that executes the program code to: search an online recipe database based on user-defined criteria; perform timeline analysis of preparation steps; merge timelines to allow the user to prepare all dishes concurrently; and generate output to provide the user with a time chart to prepare all desired dishes concurrently.

In some embodiments, the system comprises program code to infer level of involvement required from the user at each step using text analytics and machine learning approaches.

In some embodiments, the system comprises program code to search ingredient supplier databases.

In some embodiments, the system comprises program code to provide a list of ingredient suppliers.

In some embodiments, the system comprises program code to provide a total cost of ingredients.

In some embodiments, the system comprises program code to modify each recipe of the meal plan based on number of servings required.

In some embodiments, the system comprises program code to compare ingredient list for each recipe of the meal plan and ingredients user has in their pantry to generate a shopping list for any missing ingredients. Optionally, the shopping list may include supplier information for each ingredient.

In accordance with another aspect of the invention, there is provided a computer implemented method for searching recipes for meal planning, the method comprising searching an online recipe database based on user-defined criteria; performing timeline analysis of preparation steps; merging timelines to allow the user to prepare all dishes concurrently; and generating output to provide the user with a time chart to prepare all desired dishes concurrently.

In some embodiments, the method comprises inferring the number of people required to perform each consolidated recipe step using text analytics and machine learning approaches.

In some embodiments, the method comprises searching ingredient supplier databases.

In some embodiments, the method comprises providing a list of ingredient suppliers.

In some embodiments, the method comprises providing a total cost of ingredients.

In some embodiments, the method comprises modifying each recipe of the meal plan based on number of servings required. Optionally, the number of servings required may be based on number of guests, servings per guest and/or desire for leftovers.

In some embodiments, the method comprises comparing ingredient list for each recipe of the meal plan and ingredients user has in their pantry to generate a shopping list for any missing ingredients.

The method may be a website based method or an app based method.

In accordance with another aspect of the present invention, there is provided non-transitory, computer-readable storage medium comprising instructions for searching recipes for meal planning comprising computer executable instructions searching an online recipe database based on user-defined criteria; performing timeline analysis of preparation steps; merging timelines to allow the user to prepare all dishes concurrently; and generating output to provide the user with a time chart to prepare all desired dishes concurrently.

BRIEF DESCRIPTION OF FIGURES

Embodiments of the invention will now be described, by way of example only, by reference to the attached Figures, wherein:

FIG. 2 is an operation flowchart of an embodiment.

DETAILED DESCRIPTION

The present invention provides an on-line system and method for searching recipes for meal planning. The method of the present invention allows for a user to prepare multiple recipes concurrently for preparation of a meal.

Figure 1:
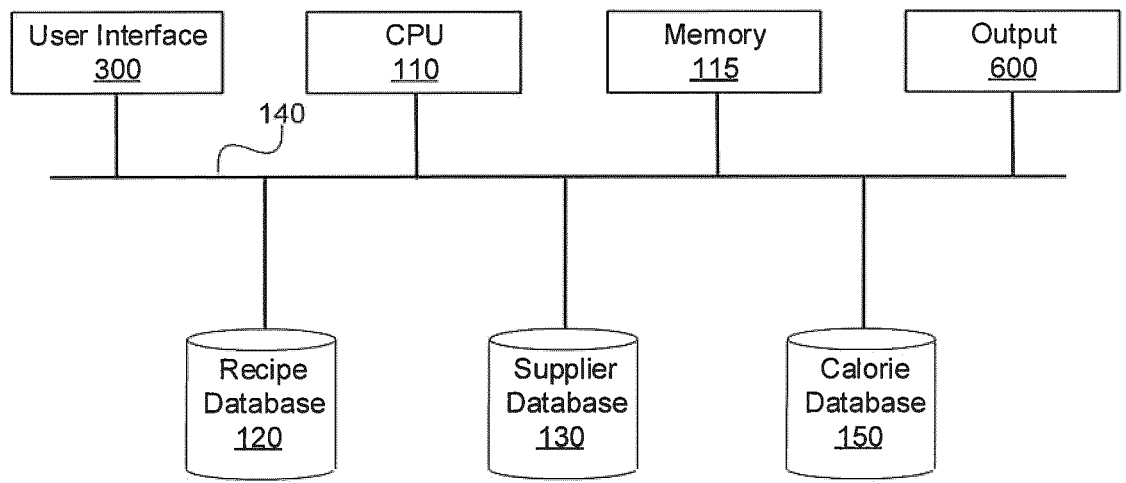
FIG. 1 is a schematic configuration of one embodiment of the meal preparation planning system.

An embodiment of the present invention is described with reference to the figures below. FIG. 1 is a schematic configuration of the meal preparation planning system of an embodiment of the invention. In this embodiment, the system includes a CPU 110 and a memory 115 that communicate 140 with user interface 300 and external databases. The system performs searches from a recipe database 120, a supplier database 130, and a calorie database 150, optionally the calorie database 150 is an on-line database, perform analysis of the search results to meet user criteria input from a user interface 300, and generates output 600 that includes displays such as timeline of meal preparation 700 and location of suppliers of ingredients.

FIG. 2 illustrates an embodiment of the invention where CPU 110 takes in user criteria through the user interface 300, and searches the recipe database 120 based on certain user criteria. In an embodiment, the CPU 110 performs analyses on the recipes and extracts ingredients required by the recipes 400. CPU 110 determines if the recipes meet user criteria 220. If not, CPU 110 goes back to perform a new recipe search 210. If all criteria are met, CPU 110 aggregates all ingredients 205 and selects ingredient suppliers 500. Output 600 is returned to the user.

Figure 3:
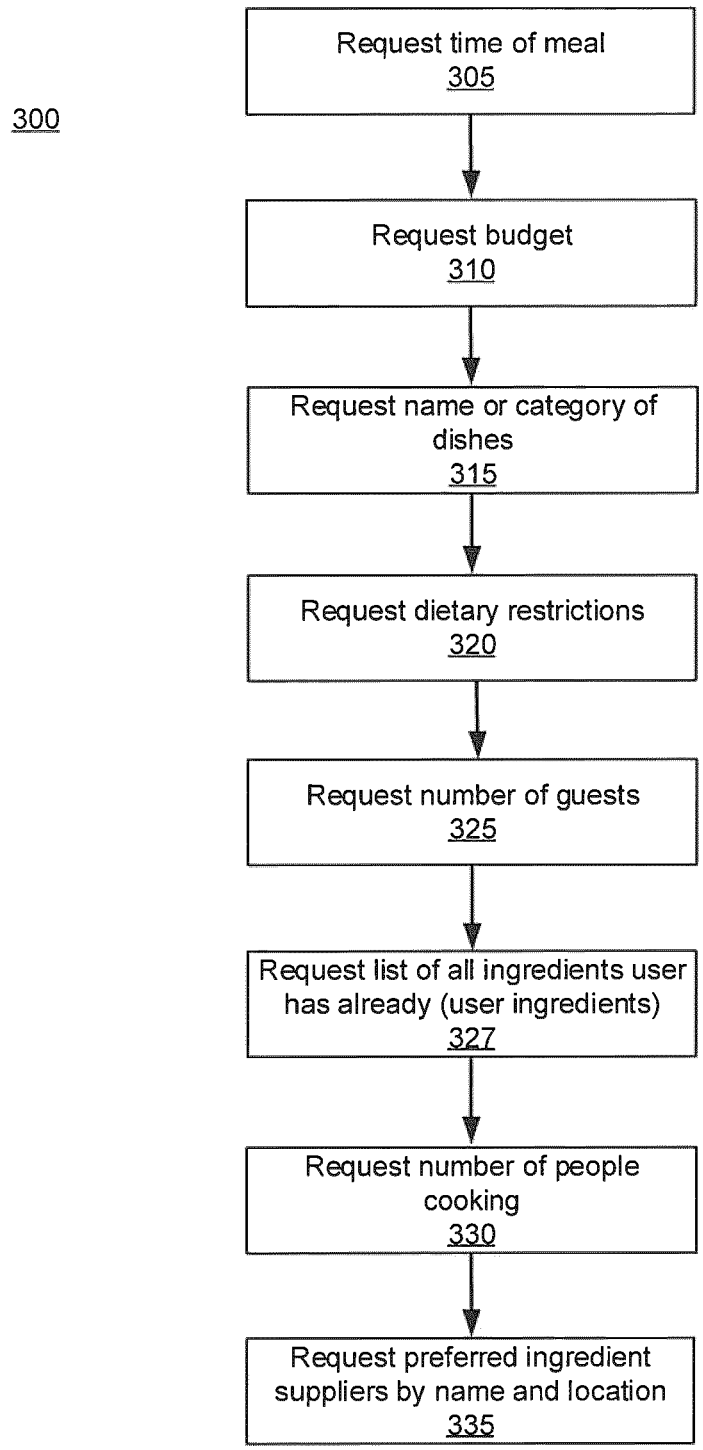
FIG. 3 illustrates examples of user criteria that the system takes in through the user interface 300.

FIG. 3 illustrates examples of user criteria that CPU 110 takes in through the user interface 300. Information the CPU 110 may request from the user include: time of the meal 305, budget 310, name or category of dishes 315, dietary restrictions 320, number of guests 325, list of ingredients user has already (user ingredients) 327, number of people cooking 330, and/or preferred ingredient suppliers by name or location 335. This is not an exhaustive list. Additional user criteria may be added. The information may be requested in any order.

Figure 4:
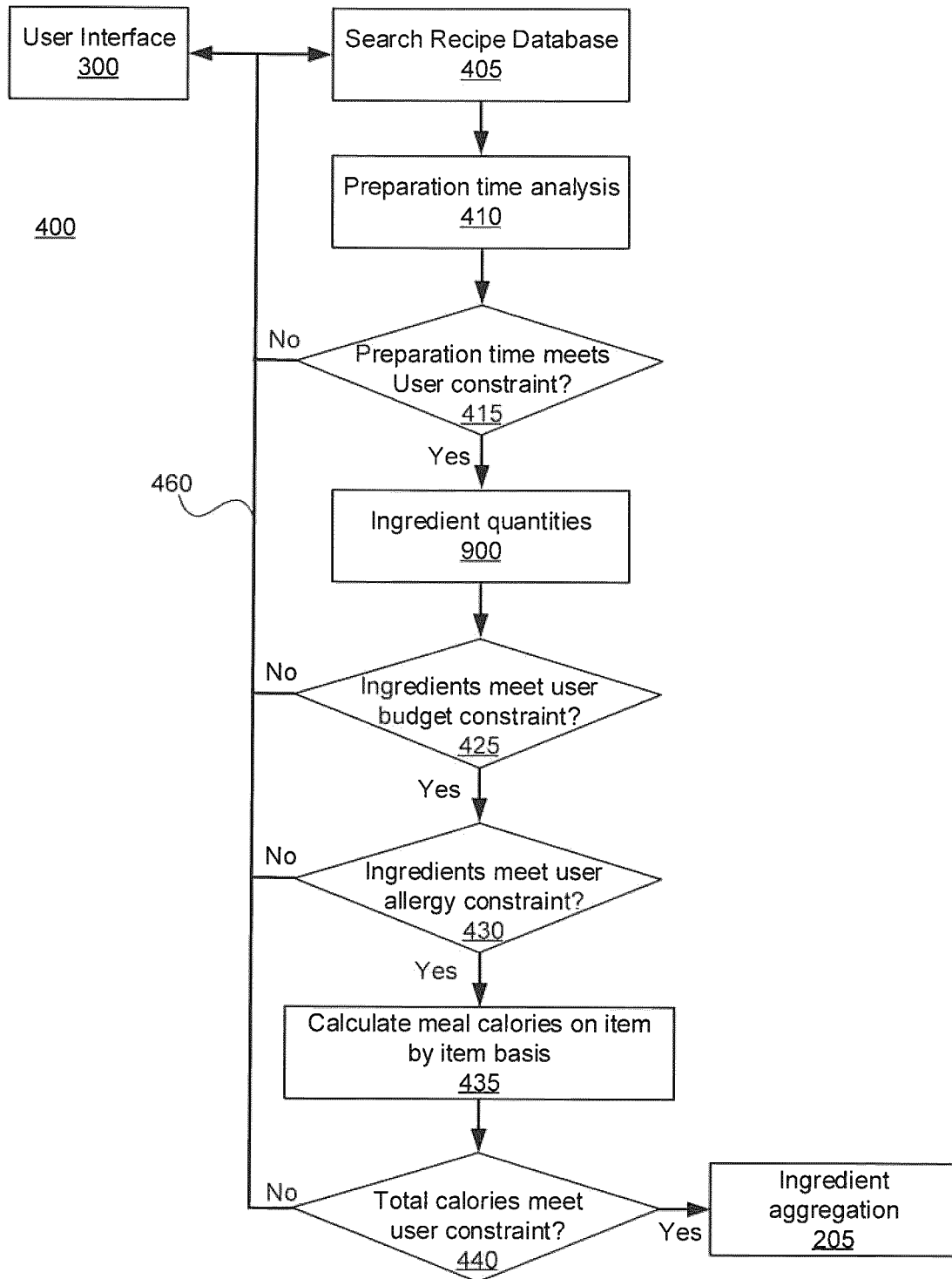
FIG. 4 illustrates the ingredient extraction process 400 that produces a list of ingredients from a set of recipes that meet all user criteria gathered through the user interface 300.

FIG. 4 illustrates the ingredient extraction process 400 of an embodiment of the invention that produces a list of ingredients from a set of recipes that meet all user criteria gathered through the user interface 300. In an embodiment, CPU 110 searches the recipe database 405 based on a subset of user criteria such as name of category of dishes 315, dietary restrictions 320, and location, including altitude, where user will prepare the meal 505. In an embodiment, CPU 110 performs preparation time analysis 410 and determines if preparation time meets user constraint 415. If preparation time does not meet constraint set by the user 460, then the CPU 110 repeats search 405 and preparation time analysis 410. If preparation time meets user constraint 435, then ingredient quantities are extracted from the selected recipes 900.

CPU 110 performs analysis to determine if the ingredients meet user budget constraint 425, user allergy constraint 430, and total calories constraint 440. If the ingredients do not meet one or more of these constraints 460, CPU 110 repeats the process from search recipe database 405 to generate a new set of recipes for analysis. The output is an aggregated list of ingredients 205.

Figure 5:
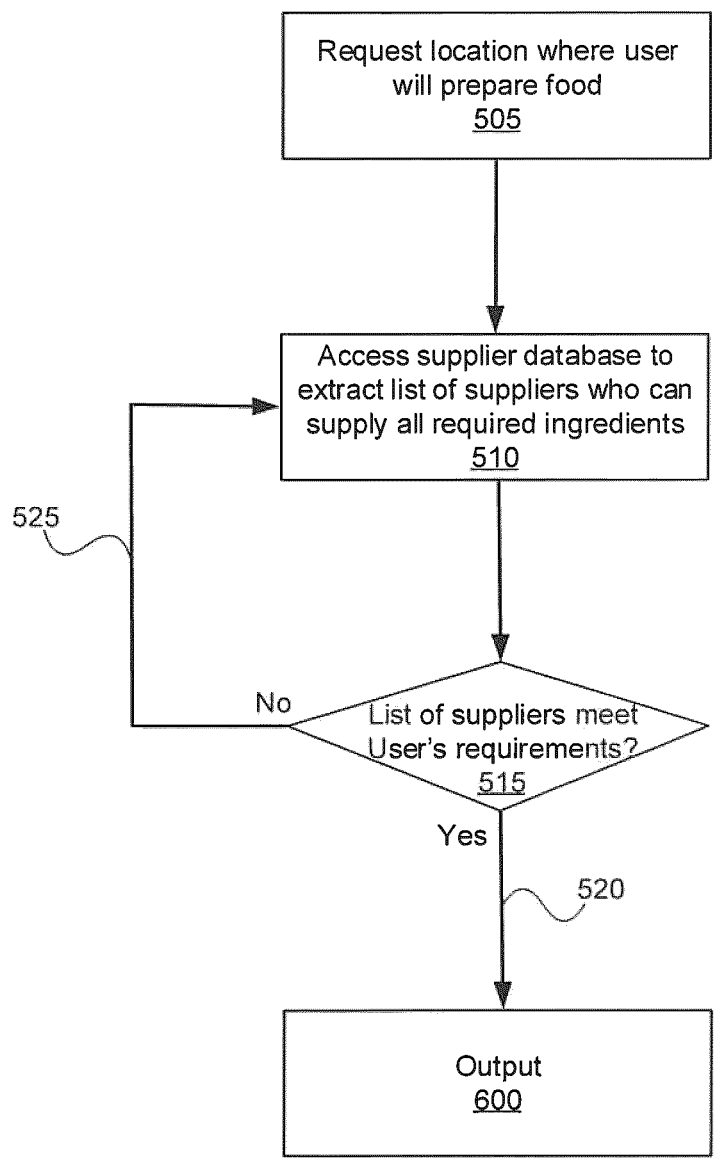
FIG. 5 illustrates the supplier selection process 500.

FIG. 5 illustrates the supplier selection process 500 of an embodiment of the invention. In this embodiment, CPU 110 requests location where user will prepare the food 505, and searches supplier database 130 for suppliers who can supply all required ingredients 510. Suppliers include a physical stores and online merchants. In an embodiment, CPU 110 calculates total cost of ingredients from each supplier returned from the search. CPU 110 then determines if the suppliers meet user requirements 515. If not 525, CPU 110 repeats the selection process. If the list of suppliers meets the user's requirements 520, CPU 110 generates output 600.

Figure 6:
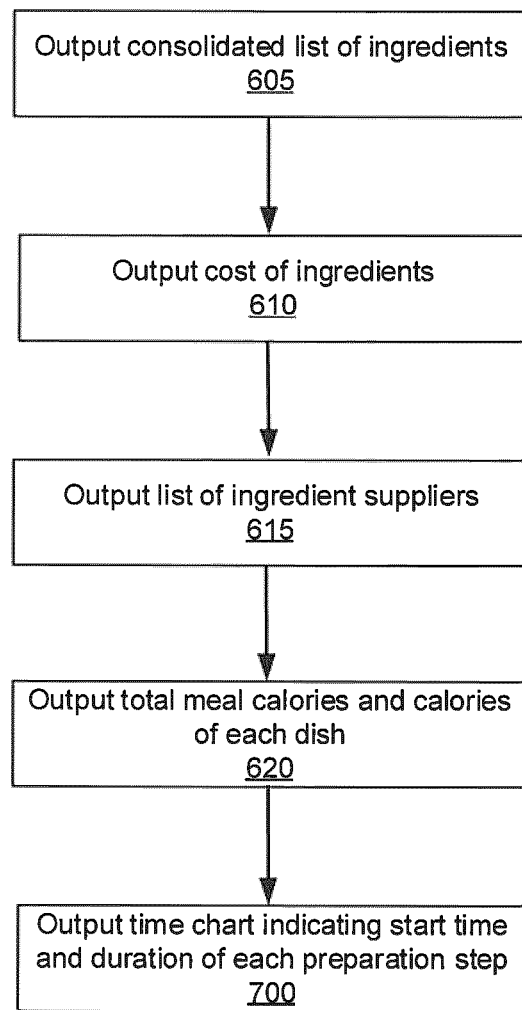
FIG. 6 illustrates outputs generated by an embodiment of the invention.

FIG. 6 illustrates the outputs generated by an embodiment of the invention. The outputs include a consolidated list of ingredients 605, the cost of ingredients 610, the list of ingredient suppliers 615, total meal calories and calories of each dish 620, and a time chart indicating start time and duration of each preparation step 700.

Figure 7:
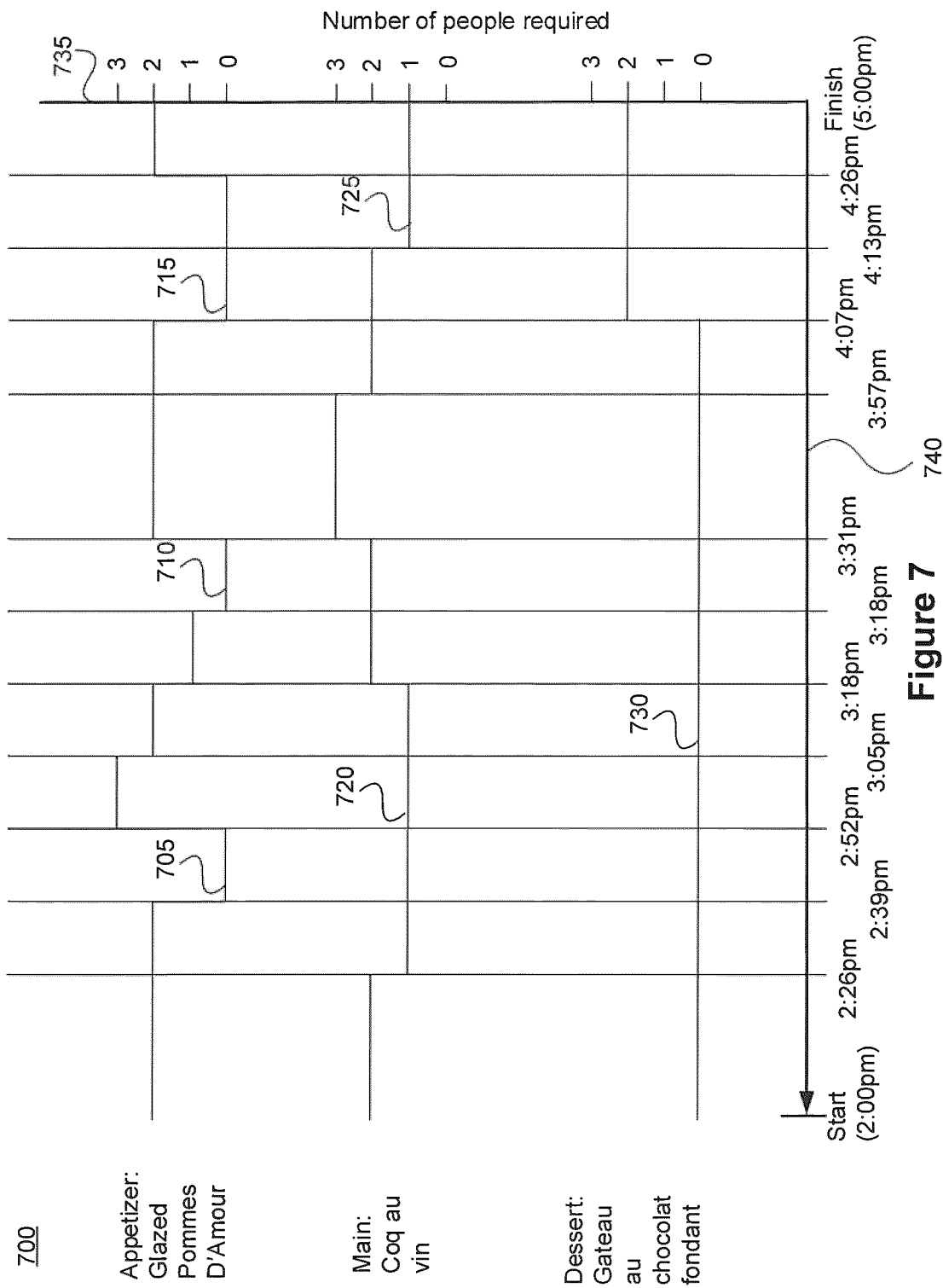
FIG. 7 illustrates an output chart generated by an embodiment of the invention.

FIG. 7 illustrates an output chart generated by an embodiment of the invention. This chart includes the consolidated recipe task start and stop times 740 for each dish and also the number of people required 735 to perform each step of the consolidated recipe. A consolidated recipe is a single recipe stating the steps required to produce the one or more selected recipes.

Figure 8:
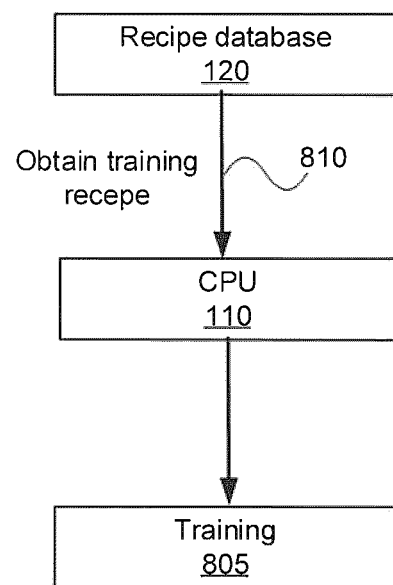
FIG. 8 illustrates a flowchart for training an embodiment of the invention to infer consolidated recipe task start and stop times and also requirement and level of involvement for each preparation step of a recipe.

FIG. 8 illustrates a method 800 of an embodiment of the invention to determine consolidated recipe task start and stop times 740 and also the number of people required for each preparation step of a consolidated recipe via training recipes. A training recipe is a recipe obtained 810 from recipe database 120. In an embodiment, CPU 110 uses the training recipe to identify tasks or blocks of tasks that require active involvement from people required 735 to prepare the consolidated recipe. These tasks or blocks of tasks are separated by gaps 705, 710, 715, 720, 725, 730 when no involvement from the user is required (e.g. baking time, marinating time). A gap is a step of the consolidated recipe when 0 people are required to perform a task.

In an embodiment, CPU 110 is trained 805 to infer precise time gaps 705, 710, 715, 720, 725, 730 (e.g. Bake for 45 minutes) and flexible time gaps (e.g. marinate in the fridge for at least two hours).

In an embodiment, CPU 110 is trained 805 to determine consolidated recipe task start and stop times 740. Factors taken into account by CPU 110 when determining task times include the nature of the task (e.g. chopping vegetables), number of ingredients, amount of each ingredient etc.

In an embodiment, CPU 110 is trained 805 to determine the level of attention or involvement required for each recipe task. An example of a recipe task is simmering for 30 minutes with occasional stirring that requires that the people required to prepare the recipe will to attend to the task intermittently. The people required to prepare the recipe will carry out another task while the food is simmering.

In an embodiment, CPU 110 is trained 805 to merge the preparation tasks and task times of each of the selected recipes to determine the minimum time required to prepare all dishes concurrently 700. In merging the preparation tasks and task start and stop times of the consolidated recipe, CPU 110 extends gaps and also inserts one or more parallel tasks if the overall preparation time of the consolidated recipe is reduced. If the preparation time of the consolidated recipe exceeds one or more of the user's criteria: number of people cooking; meal time; dietary restrictions; number of servings; budget, CPU 110 selects one or more new recipe(s) and repeats this analysis.

Figure 9:
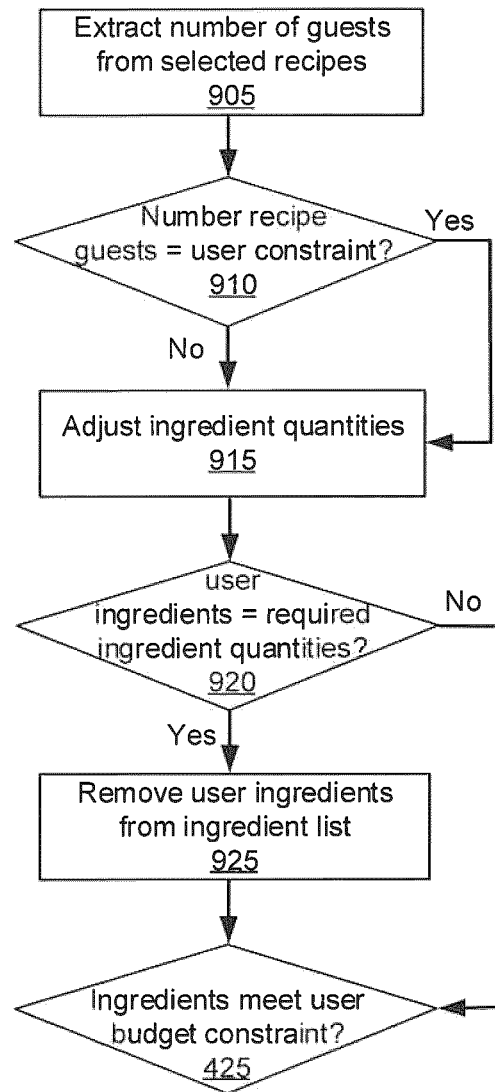
FIG. 9 illustrates an embodiment of the invention for ingredient extraction.

FIG. 9 illustrates an embodiment of the invention for ingredient quantity extraction 900. The user's selected recipes are parsed to determine the number of guests the recipe's are to serve (number recipe guests) 905. The quantity of ingredients is adjusted 915 if number recipe guests does not equal the number of guests the user has specified 910. The quantity of ingredients is decreased if the user specified number of guests is less than number recipe guests. The quantity of ingredients is increased if the user specified number of guests is greater than number recipe guests. If user ingredients contain sufficient quantities of required ingredients 920, then ingredients are removed from the list of ingredients 925.

I claim:

1. A method for searching and managing recipes for meal planning, the method comprising:
   receiving a search request including a first user-defined criteria from a user interface;
   searching one or more databases based on said first user-defined criteria;
   generating a search output including a display on said user interface in response to said search request, said search output comprising one or more recipes based on said first user-defined criteria;
   receiving a planning request from said user interface including one or more recipes selected from said recipes based on a second user-defined criteria;
   performing a step start and stop time analysis of individual preparation steps of said selected recipes in response to said planning request;
   merging step start and stop times obtained from said step start and stop time analysis for preparing said selected recipes concurrently to generate a consolidated recipe; and
   generating an output based on said consolidated recipe, said output displaying on said user interface a time chart for preparing said selected recipes concurrently, the time chart including a number of people required for each step of said consolidated recipe;
   wherein said step start and stop time analysis further comprises:
      obtaining one or more training recipes from said one or more databases for said selected recipes; and
      performing a plurality of operations, said operations configured to
         use said training recipes to identify and infer tasks or blocks of tasks of said consolidated recipe;
         use said training recipes to identify and infer a time gap between said tasks or blocks of tasks of said consolidated recipe, wherein during said time gap zero people are required to perform one of said tasks or blocks of tasks;
         said training recipes are further used to extend said time gap to insert one or more parallel tasks to optimize said consolidated recipe.

2. The method of claim 1, wherein searching said databases includes searching an ingredient supplier database, a recipe database, and a calorie database.

3. The method of claim 1 further comprising providing a list of ingredient suppliers.

4. The method of claim 1 further comprising providing a total cost of ingredients.

5. The method of claim 1 further comprising modifying one of said selected recipes based on a number of servings required.

6. The method of claim 1 further comprising comparing an ingredient list for each selected recipe with ingredients in a user pantry to generate a shopping list for any missing ingredients.

7. The method of claim 1, wherein said method includes a website based method or an app based method.

8. The method of claim 1, wherein said tasks or blocks of tasks of said consolidated recipe is performed intermittently.

9. The method of claim 1, wherein said time gap includes a precise time gap or a flexible time gap.

10. A method for selecting training recipes for meal planning, the method comprising:
    obtaining one or more training recipes from one or more databases for selected recipes;
    using said selected training recipes to generate a consolidated recipe, by performing a step start and stop time analysis of individual preparation steps of said selected training recipes, said analysis comprising:
       using said selected training recipes to identify and infer tasks or blocks of tasks of said consolidated recipe;
       using said selected training recipes to identify and infer a time gap between said tasks or blocks of tasks of said consolidated recipe, wherein during said time gap zero people are required to perform one of said tasks or blocks of tasks;
       use said selected training recipes to determine said step start and stop times in said consolidated recipe; and
       use said selected training recipes to optimize said consolidated recipe, said optimization determining a minimum time required to prepare said consolidated recipe; and
    said selected training recipes are further used to extend said time gap to insert one or more parallel tasks to optimize said consolidated recipe.

11. A non-transitory, computer-readable storage medium comprising instructions for searching and managing recipes for meal planning, said instructions comprising computer executable instructions for:
    receiving a search request including a first user-defined criteria from a user interface;
    searching one or more databases based on said first user-defined criteria;
    generating a search output including a display on said user interface in response to said search request, said search output comprising one or more recipes based on said first user-defined criteria;
    receiving a planning request from said user interface including one or more recipes selected from said recipes based on second user-defined criteria;
    performing a step start and stop time analysis of individual preparation steps of said selected recipes in response to said planning request;
    merging step start and stop times obtained from said step start and stop time analysis for preparing said selected recipes concurrently to generate a consolidated recipe; and
    generating an output based on said consolidated recipe, said output displaying on said user interface a time chart for preparing said selected recipes concurrently, the time chart including a number of people required for each step of said consolidated recipe;
    wherein said step start and stop time analysis further comprises:

performing a plurality of operations, said operations configured to
  use said selected recipes to identify and infer tasks or blocks of tasks of said consolidated recipe;
  use said selected recipes to identify and infer a time gap between said tasks or blocks of tasks of said consolidated recipe, wherein during said time gap zero people are required to perform one of said tasks or blocks of tasks;
  said selected recipes are further used to extend said time gap to insert one or more parallel tasks to optimize said consolidated recipe.

12. The non-transitory, computer-readable storage medium of claim 11, wherein said time gap is one of a precise time gap or a flexible time gap.

13. A non-transitory, computer-readable storage medium, comprising instructions for selecting training recipes for meal planning, said instructions comprising computer executable instructions for:
  obtaining one or more training recipes from one or more databases for selected recipes;
  using said selected training recipes to generate a consolidated recipe, by performing a step start and stop time analysis of individual preparation steps of said selected training recipes, said analysis comprising:
    using said selected training recipes to identify and infer tasks or blocks of tasks of said consolidated recipe;
    using said selected training recipes to identify and infer a time gap between said tasks or blocks of tasks of said consolidated recipe, wherein during said time gap zero people are required to perform one of said tasks or blocks of tasks;
    use said selected training recipes to determine said step start and stop times in said consolidated recipe; and
    use said selected training recipes to optimize said consolidated recipe, said optimization determining a minimum time required to prepare said consolidated recipe; and
  said selected training recipes are further used to extend said time gap to insert one or more parallel tasks to optimize said consolidated recipe.

* * * * *

UNITED STATES PATENT AND TRADEMARK OFFICE
CERTIFICATE OF CORRECTION

PATENT NO. : 12,164,581 B2  
APPLICATION NO. : 18/216796  
DATED : December 10, 2024  
INVENTOR(S) : Chris Knight Page 1 of 1

It is certified that error appears in the above-identified patent and that said Letters Patent is hereby corrected as shown below:

On the Title Page

In Column 1, Page 2, change "Lerullo" to -- Ierollo --.

In the Specification

In Column 4, Lines 8-9, change "Suppliers include a physical stores and online merchants." to -- Suppliers include physical stores and online merchants. --.

In Column 4, Line 56, change "required to prepare the recipe will to attend to the task" to -- required to prepare the recipe will attend to the task --.

In the Claims

In Claim 8, Column 6, Lines 10-11, change "The method of Claim 1, wherein said tasks or blocks of tasks of said consolidated recipe is performed intermittently." to -- The method of Claim 1, wherein said tasks or blocks of tasks of said consolidated recipe are performed intermittently. --.

Signed and Sealed this  
Twenty-eighth Day of January, 2025

Coke Morgan Stewart  
*Acting Director of the United States Patent and Trademark Office*